United States Patent
Rooks

(10) Patent No.: US 11,058,489 B2
(45) Date of Patent: Jul. 13, 2021

(54) DEVICES, SYSTEMS, AND METHODS FOR A MICROWAVE ABLATION PROCEDURE

(71) Applicant: Covidien LP, Mansfield, MA (US)

(72) Inventor: Kathy E. Rooks, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 583 days.

(21) Appl. No.: 15/892,702

(22) Filed: Feb. 9, 2018

(65) Prior Publication Data

US 2018/0228543 A1 Aug. 16, 2018

Related U.S. Application Data

(60) Provisional application No. 62/457,246, filed on Feb. 10, 2017.

(51) Int. Cl.
*A61B 18/18* (2006.01)
*A61B 18/00* (2006.01)
(Continued)

(52) U.S. Cl.
CPC .............. *A61B 18/1815* (2013.01); *A61B 2018/00023* (2013.01); *A61B 2018/00273* (2013.01); *A61B 2018/00285* (2013.01); *A61B 2018/00529* (2013.01); *A61B 2018/00541* (2013.01); *A61B 2018/00577* (2013.01); *A61B 2018/00642* (2013.01); *A61B 2018/00666* (2013.01); *A61B 2018/00678* (2013.01); *A61B 2018/00708* (2013.01); *A61B 2018/00744* (2013.01); *A61B 2018/00791* (2013.01); *A61B 2018/00863* (2013.01); *A61B 2018/1823* (2013.01); *A61B 2018/1861* (2013.01); *A61B 2018/1892* (2013.01); *A61M 25/0045* (2013.01);
(Continued)

(58) Field of Classification Search
CPC ...... A61B 18/1815; A61B 2018/00023; A61B 2018/00273; A61B 2018/00285; A61B 2018/00577; A61B 2018/00642; A61B 2018/00666; A61B 2018/00678; A61B 2018/00708; A61B 2018/00744; A61B 2018/00863; A61B 2018/1823; A61B 2018/1892; A61B 18/00–28; A61B 2018/00005–266; A61M 2025/1059; A61M 2205/3331; A61M 25/0045; A61M 25/10182

See application file for complete search history.

(56) References Cited

U.S. PATENT DOCUMENTS 6,188,355 B1 2/2001 Gilboa
2003/0176758 A1* 9/2003 Nakano ............ A61N 5/1002
600/3
(Continued)

FOREIGN PATENT DOCUMENTS

WO 00/10456 A1 3/2000
WO 01/67035 A1 9/2001
WO 2017/151342 A1 9/2017

*Primary Examiner* — Daniel W Fowler

(57) ABSTRACT

Microwave ablation devices and systems and method including the devices are provided. The microwave ablation device includes a cable assembly operably coupled to an energy source, a feedline in electrical communication with the cable assembly, a balun disposed on the feedline, an outer tubular member through which the feedline at least partially extends, and an inflatable barrier disposed on the outer tubular member proximal to the balun.

20 Claims, 10 Drawing Sheets

(51) Int. Cl.
*A61M 25/10* (2013.01)
*A61M 25/00* (2006.01)

(52) U.S. Cl.
CPC ... *A61M 25/0097* (2013.01); *A61M 25/10182* (2013.11); *A61M 2025/1059* (2013.01); *A61M 2205/3331* (2013.01); *A61M 2205/50* (2013.01)

(56) References Cited

U.S. PATENT DOCUMENTS

| | | | |
|---|---|---|---|
| 2013/0345553 A1* | 12/2013 | Arts | A61B 18/1492 600/424 |
| 2014/0046174 A1 | 2/2014 | Ladtkow et al. | |
| 2014/0046315 A1 | 2/2014 | Ladtkow et al. | |
| 2014/0081254 A1* | 3/2014 | Rudie | A61B 18/1815 606/27 |
| 2014/0270441 A1 | 9/2014 | Baker | |
| 2014/0276033 A1 | 9/2014 | Brannan et al. | |
| 2014/0281961 A1 | 9/2014 | Baker | |
| 2014/0282216 A1 | 9/2014 | Baker | |
| 2015/0141809 A1 | 5/2015 | Costello et al. | |
| 2015/0141869 A1 | 5/2015 | Costello et al. | |
| 2015/0265257 A1 | 9/2015 | Costello et al. | |
| 2015/0343136 A1* | 12/2015 | Nitzan | A61M 1/3653 604/6.09 |
| 2017/0202543 A1 | 7/2017 | Herdina et al. | |
| 2017/0245740 A1 | 8/2017 | Krimsky et al. | |

\* cited by examiner

DEVICES, SYSTEMS, AND METHODS FOR A MICROWAVE ABLATION PROCEDURE

CROSS-REFERENCE TO RELATED APPLICATIONS

This application claims the benefit of U.S. Provisional Application Ser. No. 62/457,246, filed on Feb. 10, 2017, the entire contents of which are incorporated by reference herein.

BACKGROUND

1. Technical Field

The present disclosure relates to microwave surgical devices and systems suitable for use in tissue ablation applications.

2. Discussion of Related Art

Treatment of certain diseases requires the destruction of malignant tissue growths, e.g., tumors. In this regard, electrosurgical devices utilizing electromagnetic radiation have been developed to heat and kill tumor cells. For example, apparatus for use in ablation procedures include a power generation source, e.g., a microwave or radio frequency (RF) electrosurgical generator that functions as an energy source, and a surgical instrument (e.g., ablation probe having an antenna assembly) for directing energy into the target tissue. The generator and surgical instrument are typically operatively coupled by a cable assembly having a plurality of conductors for transmitting energy from the generator to the instrument, and for communicating control, feedback and identification signals between the instrument and the generator.

During treatment, the ablation probe may be inserted into tissues where cancerous tumors have been identified. Once the probe is positioned, electrosurgical energy is passed through the probe and into surrounding tissue to form an "active zone." The energy applied to the tissue denatures the cancerous cells with heat. With recent advancements in ablation technology, the active zone in which ablative energy is output can be more precisely controlled. For example, the ablative energy is confined to a tip portion of the probe and hence, does not radiate back along the length of the probe proximal to the tip as in previous configurations. As a result, the surgeon can perform the ablative procedure with more specificity and more accurately ablate targeted tissue. Although these types of treatments are effective, they may be improved.

SUMMARY

According to an aspect of the present disclosure, an energy-delivery device suitable for delivery of energy to tissue is provided. In an embodiment, a microwave ablation device is provided and includes a feedline, an antenna assembly, an outer tubular member, and an inflatable barrier. The feedline is in electrical communication with an energy source. The antenna assembly is coupled to the feedline and includes a radiating portion. The outer tubular member at least partially extends through the feedline. The inflatable barrier is disposed on the outer tubular member proximal to the radiating portion of the antenna assembly.

In an aspect of the present disclosure, the inflatable barrier is formed as a portion of the outer tubular member.

In another aspect of the present disclosure, the outer tubular member includes a first material and a second material that has a higher elastic modulus than the first material, and the inflatable barrier is made of the first material.

In another aspect of the present disclosure, the outer tubular member is multi-layered and includes an outer layer and an inner layer, the outer layer includes a first material and the inner layer includes a second material that is more expandable than the first material, and the outer layer includes a gap exposing a portion of the inner layer forming the inflatable barrier.

In another aspect of the present disclosure, the microwave ablation device further includes a hub including a port configured to be coupled to a cooling pump to pressurize a lumen defined by the outer tubular member, wherein the inflatable barrier is configured to expand in response to pressurization of the lumen, and the inflatable barrier deflates in response to depressurization of the lumen.

In another aspect of the present disclosure, the microwave ablation device further includes an outer sheath extending along a portion of the outer tubular member, wherein the inflatable barrier is formed as a portion of the outer sheath.

In another aspect, the microwave ablation device further includes a hub including a port configured to be coupled to a pump to pressurize a lumen defined by the outer sheath, wherein the inflatable barrier is configured to expand in response to pressurization of the lumen, and the inflatable barrier is configured to deflate in response to depressurization of the lumen.

According to another embodiment, a system is provided for performing a microwave ablation procedure. The system includes an electrosurgical generator, a cooling fluid pump, and a microwave ablation device. The microwave ablation device includes a cable assembly, a feedline, an antenna assembly, an outer tubular member, and an inflatable barrier. The cable assembly is operably coupled to the electrosurgical generator. The feedline is in electrical communication with the cable assembly. The antenna assembly is coupled to the feedline and includes a radiating portion. The outer tubular member at least partially extends through the feedline, and the inflatable barrier is disposed on the outer tubular member proximal to the radiating portion of the antenna assembly.

In another aspect, the inflatable barrier is formed as a portion of the outer tubular member, the microwave ablation device further includes a hub including a port in communication with a lumen defined by the outer tubular member, and the cooling fluid pump is configured to pressurize the lumen defined by the outer tubular member, wherein the inflatable barrier is configured to expand in response to pressurization of the lumen, and the inflatable barrier is configured to deflate in response to depressurization of the lumen.

In another aspect, the system also includes a computing device including a processor and a memory storing instructions which, when executed by the processor, cause the computing device to start the cooling fluid pump to pressurize the lumen and thereby expand the inflatable barrier, detect a pressure within the lumen, and generate electrosurgical energy using the electrosurgical generator to deliver microwave energy to the feedline, based upon the detected pressure within the lumen being greater than a threshold pressure.

In another aspect, the microwave ablation device further includes an outer sheath extending along a portion of the outer tubular member, wherein the inflatable barrier is formed as a portion of the outer sheath, and the system further comprises a hub including an opening in communication with a lumen defined by the outer sheath, and a pump coupled to the hub configured to pressurize the lumen defined by the outer sheath, wherein the inflatable barrier is configured to expand in response to pressurization of the lumen, and the inflatable barrier is configured to deflate in response to depressurization of the lumen.

In another aspect of the present disclosure, a computing device is included a processor and a memory storing instructions which, when executed by the processor, cause the computing device to start the pump to pressurize the lumen and thereby expand the inflatable barrier, detect a pressure within the lumen, and generate electrosurgical energy using the electrosurgical generator to deliver microwave energy to the feedline, based upon the detected pressure within the lumen being greater than a set threshold pressure.

In still another aspect, the memory stores further instructions which, when executed by the processor, cause the computing device to, deflate the inflatable barrier based upon a detection of the microwave energy not being delivered to the feedline to thereby cause the lumen to be de-pressurized.

In another aspect of the present disclosure, the pump includes a syringe.

According to another aspect, a method is provided of controlling a microwave ablation device. The method includes pressurizing a lumen formed by outer tubular member of the microwave ablation device to inflate an inflatable barrier disposed proximal to a balun of a microwave antenna assembly, detecting a pressure within the lumen, and generating electrosurgical energy using the electrosurgical generator to deliver microwave energy to the microwave antenna assembly based upon the detected pressure within the lumen being greater than a threshold pressure.

In another aspect, the pressurizing includes supplying cooling fluid to the lumen from a cooling pump.

In another aspect, the method further includes deflating the inflatable barrier based upon detecting the microwave energy not being delivered to the microwave antenna assembly to thereby cause the lumen to be de-pressurized.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, of which.

DETAILED DESCRIPTION

Figure 1:
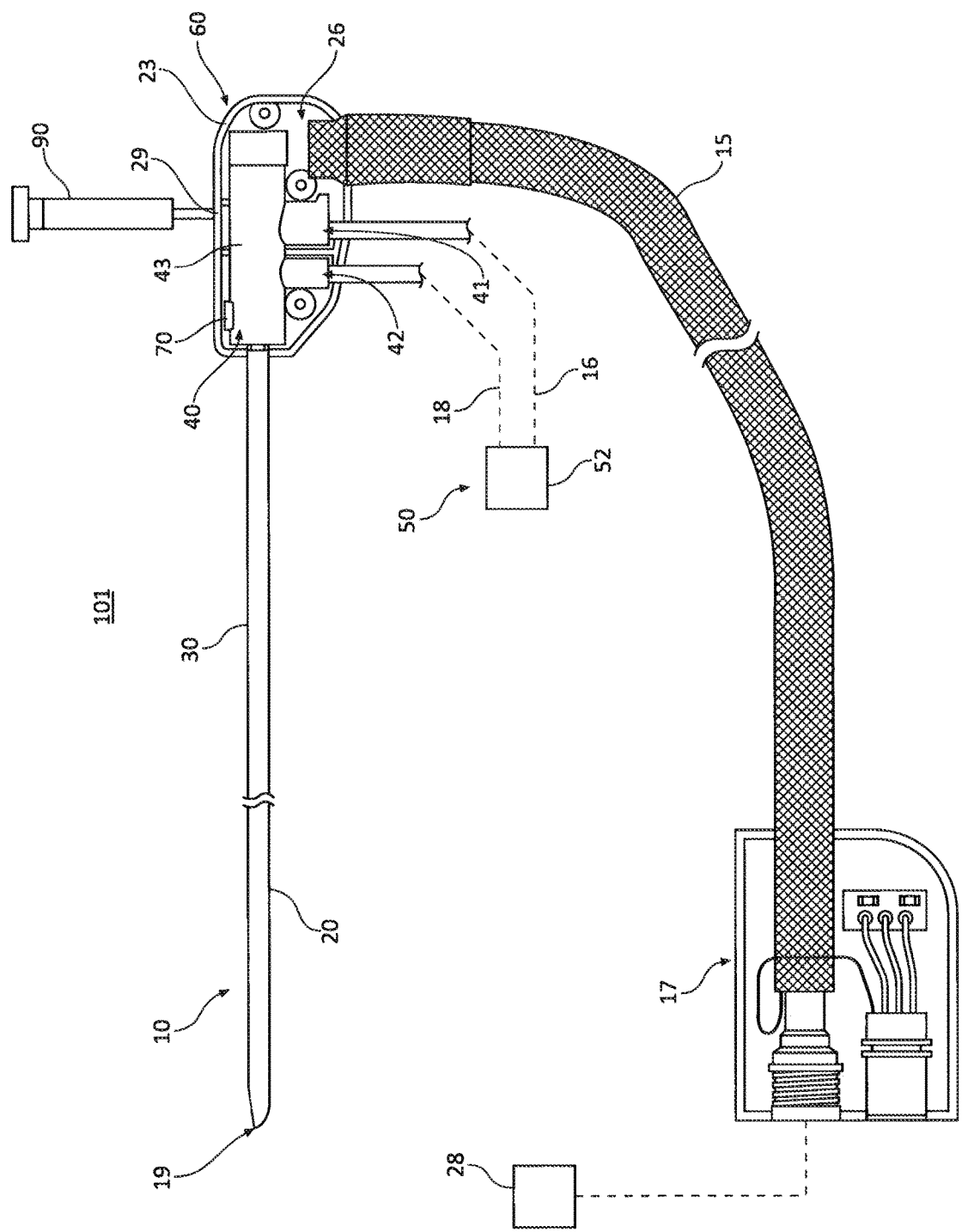
FIG. 1 is a schematic diagram of a microwave ablation system in accordance with an illustrative embodiment of the present disclosure.

The present disclosure is directed generally to microwave ablation devices, and to systems and methods of using the devices and system to treat tissue. For example, the devices, systems, and methods may be used during treatment within a lung, liver or other solid tissue, such that an active zone of ablative energy is controlled at a tip of the device and does not migrate proximally along a shaft of the device. In this regard, steam generated as a by-product of the heat from the ablation procedure is prevented from travelling along the device shaft, which minimizes the potential for thermally fixing an opening into the lung or liver tissue. As a result, the likelihood of creating a permanent hole along the needle track is reduced. In lung ablations, this could reduce the possible risk of pneumothorax following the treatment.

One aspect of the present disclosure includes a microwave ablation device having a tubular member and an inflatable barrier near a distal portion of the tubular member proximal to a radiating portion of the device. The inflatable barrier may be formed as part of the tubular member within which a feedline of the ablation device is disposed and is configured to be expandable radially. The tubular member defines a lumen that may be pressurized by an inflation device coupled to the microwave ablation device. The pressurization of the lumen causes the inflatable barrier to expand radially. In an embodiment, the lumen is a cooling lumen, which is configured to communicate with a cooling pump for delivery of cooling fluid through the microwave ablation device. In this regard, as the cooling fluid is circulated through the microwave ablation device, the cooling fluid may exert pressure on an interior surface of the tubular member and cause the inflatable barrier to expand. In another embodiment, the inflatable barrier is formed as part of an outer sheath within which the microwave ablation device is disposed. The outer sheath and microwave ablation device define the lumen therebetween, and the inflation device may be a separate air or fluid pump for pressurizing the lumen.

Although contemplated to be implemented in the lung, the embodiments described herein are not limited to application of any particular tissue or organ for treatment, indeed, it is contemplated that the systems and methods of the present disclosure may be used to treat liver tissue, kidney tissue, pancreatic tissue, gastrointestinal tissue, interstitial masses, and other portions of the body known to those of skill in the art to be treatable via microwave ablation. These and other aspects of the present disclosure are described in greater detail below.

Hereinafter, embodiments of energy-delivery devices with a fluid-cooled probe assembly and systems including the same of the present disclosure are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the apparatus, or component thereof, closer to the user and the term "distal" refers to that portion of the apparatus, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as, for example, microwave ablation, radiofrequency (RF) ablation, or microwave or RF ablation-assisted resection.

Turning now to FIG. 1, a medical device 10 is illustrated as being incorporated into an operational system 101 having a microwave generator 28 and a coolant supply system 50. The medical device 10 includes a probe assembly 20 and a handle assembly 60. To operate the probe assembly 20 within the system 101, the probe assembly 20 is operably coupled by a cable assembly 15 to a connector assembly 17. The connector assembly 17 is a cable connector suitable to operably connect the medical device 10 to an energy source, such as the microwave generator 28. The connector may house a memory (e.g., an EEPROM) storing a variety of information regarding the cable assembly 15 and the medical device 10. For example, the memory may include identification information that can be used by the microwave generator 28 to ensure that only properly identified medical devices 10 are connected thereto. In addition, the memory may store operating parameters of the medical device 10 (e.g., time, power, and dosage limits), cable compensation parameters of the cable assembly 15, and information regarding the usage of the medical device 10 or the cable assembly 15. Usage monitoring may enable limiting re-use of the medical device 10 beyond a certain number of energizations or a single use of the device. Such usage limitations may optionally be reset via reprocessing as is commonly understood in the art. Still further, the connector assembly 17 may include sensor electronics related to radiometry and temperature sensing.

The probe assembly 20 generally includes an outer tubular member 30, an inner tubular member 35 (shown in FIG. 2), a feedline 14, a distal portion 12 including an antenna assembly 11, and a tip 19 shown in FIG. 1. The handle assembly 60 generally includes a handle body 23 defining a handle-body chamber 26 therein. Optionally, the handle body 23 is configured to permit attachment of an air pump 90 thereto. The medical device 10 also includes a hub 40 (as well as other components described herein) disposed, at least in part, within the handle-body chamber 26.

The handle body 23 includes two housing halves, which may be assembled together with the aid of alignment pins, snap-like interfaces, tongue and groove interfaces, locking tabs, adhesive ports, etc., utilized either alone or in combination for assembly purposes. The handle body 23 includes various openings 24, 25 for receiving connectors from the coolant supply system 50 and an opening 27 for receiving connectors from the microwave generator 28. The openings 24, 25, 27 may include sealing elements.

The hub 40 includes a hub body 43 defining a hub-body chamber 46 therein. The medical device 10 includes a hub cap 150 and a hub divider 160, which are configured to be receivable within the hub-body chamber 46 in sealing engagement with the inner walls of the hub body 43. The outer tubular member 30, the inner tubular member 35, the hub 40, and the components cooperative therewith (e.g., hub cap 150 and hub divider 160) are adapted to maintain fluid flow to the distal portion 12. The hub body 43 generally includes a first port 41 and a second port 42, e.g., to allow fluid communication with a coolant supply system (e.g., coolant supply system 50) via one or more coolant paths (e.g., first coolant path 16 and second coolant path 18). The first port 41 and the second port 42 may be of any suitable shape, e.g., rectangular, cylindrical, etc., and may include a groove adapted to receive an o-ring or other suitable sealing element.

In an embodiment, the hub body 43 may include one or more mechanical interfaces, for example, recess 45, adapted to matingly engage with one or more corresponding mechanical interfaces (e.g., tab 70) associated with the handle body 23, for example, to align the hub 40 within the handle body 23 and/or to fixedly secure the hub 40 within the handle-body chamber 26. A hub divider 160 is configured and utilized to divide the hub-body chamber 46 into a first chamber, for example, disposed in fluid communication with the first port 41, and a second chamber, e.g., disposed in fluid communication with the second port 42. The first chamber (for example, first chamber 147) generally fluidly connects the first port 41 to the inner tubular member 35. A pressure sensor 149 is disposed in the first chamber 147 to sense the pressure therein and to provide the readings to the connector assembly 17 via a pressure sensor wire 151. The second chamber (for example, second chamber 143) generally fluidly connects the second port 42 to the outer tubular member 30.

Figure 3:
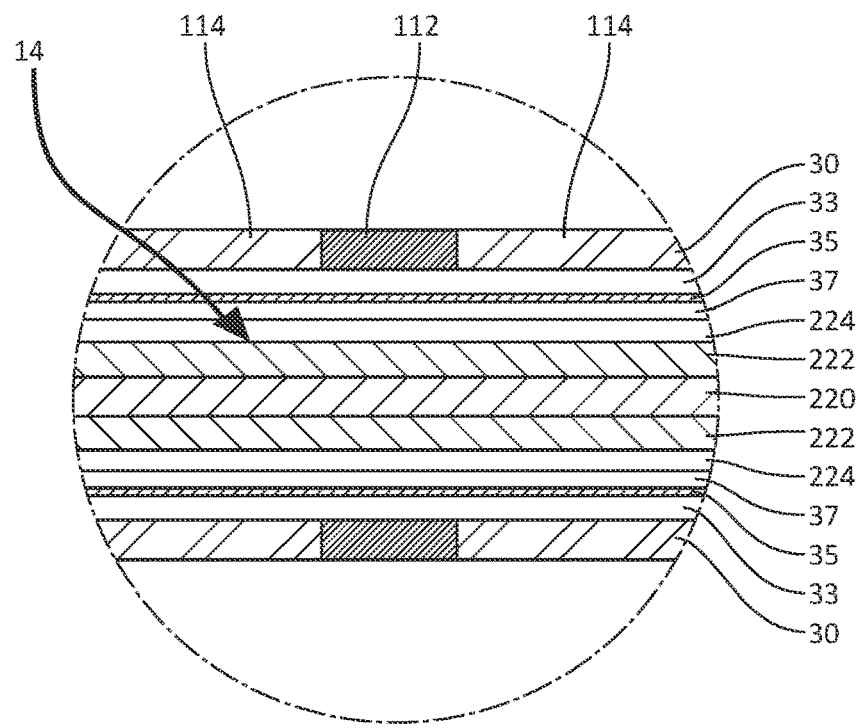
FIG. 3 is an enlarged, cross-sectional view of a portion of a probe assembly for use in the medical device of FIG. 2A including an inflatable barrier in a collapsed configuration, in accordance with an embodiment of the present disclosure.

With additional reference to FIG. 3, the outer tubular member 30 may be made of a non-conductive material and is coaxially disposed around the inner tubular member 35 defining a lumen 33 therebetween. The inner tubular member 35 is coaxially disposed around the feedline 14 and defines another lumen 37 therebetween. The inner tubular member 35 may be formed of any suitable non-electrically-conductive material, such as, for example, polymeric or ceramic materials.

In accordance with an embodiment, an inflatable barrier 112 is disposed on the outer tubular member 30. The inflatable barrier 112 may be formed as part of the outer tubular member 30, in an embodiment. For example, the outer tubular member 30 includes the inflatable barrier 112 along with non-inflatable sections 114. To permit the inflatable barrier 112 to expand relative to the non-inflatable sections 114 when fluid in the lumen 33 exerts pressure on an inner surface of the inflatable barrier 112, the inflatable barrier 112 is made up of a material with an elastic modulus selected for an ability to expand in response pressurization of the lumen 33 of greater than 60 psi, while the non-inflatable section 114 is made up of a less expandable, higher elastic modulus material. Examples of suitable materials for the inflatable barrier 112 include, but are not limited to low elastic modulus thermoplastic elastomer materials. Examples of suitable materials for the non-inflatable sections 114 include, but are not limited to high elastic modulus polymeric materials.

Figure 4:
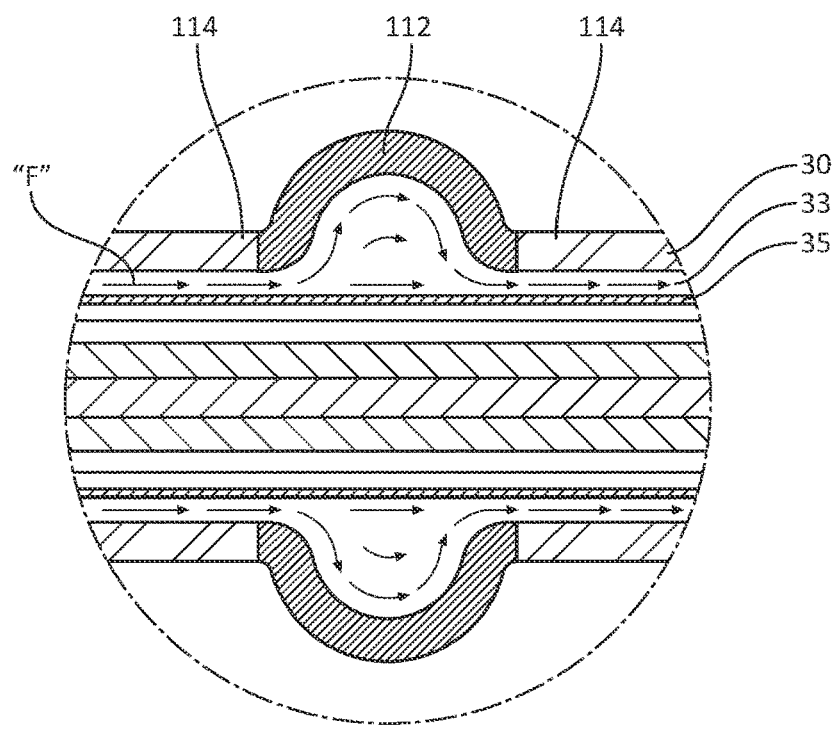
FIG. 4 is the enlarged, cross-sectional view of the portion of the probe assembly depicted in FIG. 3 including the inflatable barrier in an expanded configuration, in accordance with an embodiment of the present disclosure.

As noted briefly above, the inflatable barrier 112 is configured to expand radially outward in response to pressurization of the lumen 33 by fluid "F", as depicted in FIG. 4 in an expanded configuration. The inflatable barrier 112, and hence, the outer tubular member 30 may be configured in any one of numerous manners to form the barrier. In an embodiment of the present disclosure, the outer tubular member 30 is formed of a single continuous material, where the material forming the inflatable barrier 112 is of a first elastic modulus and the material forming the non-inflatable sections 114 is of a second elastic modulus, which may be higher than the first elastic modulus. In another embodiment of the present disclosure, the inflatable barrier 112 is a ring of material of a first elastic modulus, with each of the ends of the ring sealingly coupled to or otherwise sealingly engaged with ends of tubular non-inflatable sections 114 made of a second elastic modulus material.

Figure 5:
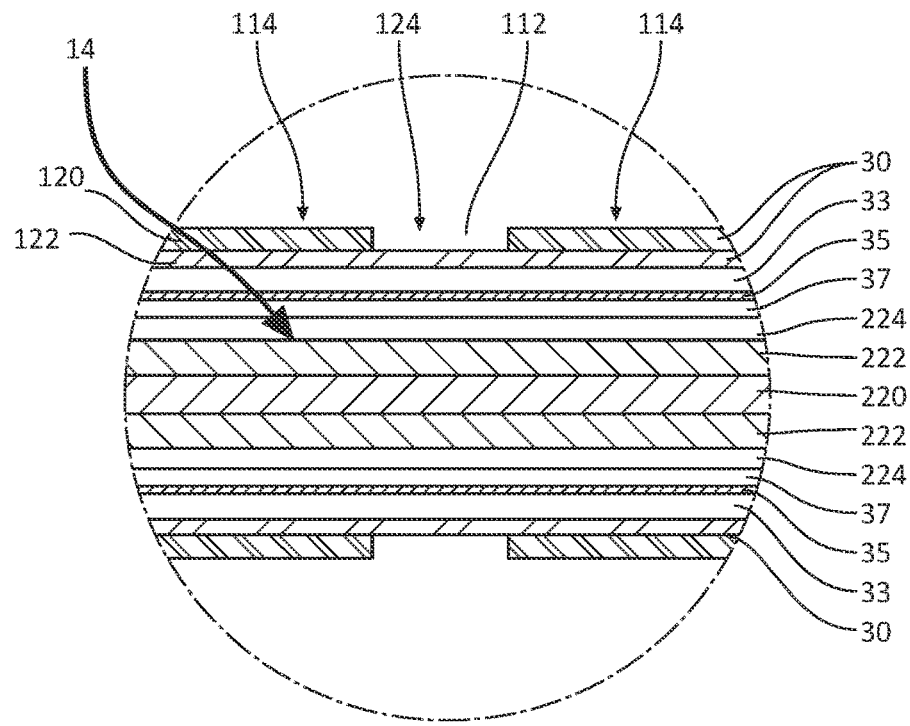
FIG. 5 is an enlarged, cross-sectional view of a portion of the probe assembly including an inflatable barrier in a collapsed configuration, in accordance with another embodiment of the present disclosure.
Figure 6:
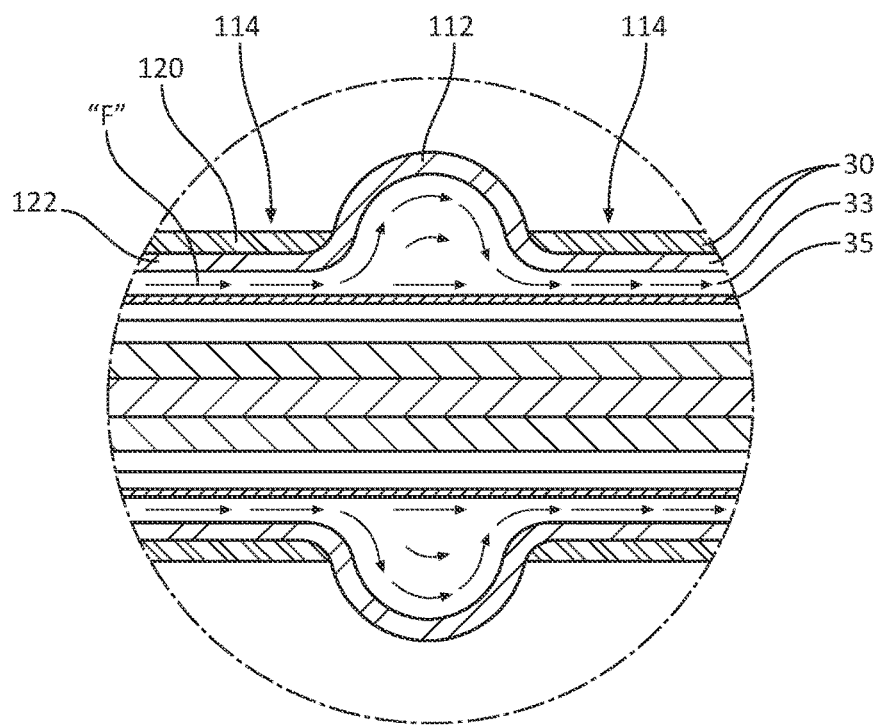
FIG. 6 is the enlarged, cross-sectional view of the portion of the probe assembly depicted in FIG. 5 including the inflatable barrier in an expanded configuration, in accordance with an embodiment of the present disclosure.

In another embodiment of the inflatable barrier 112, as depicted in FIG. 5, the outer tubular member 30 is multi-layered and includes an outer layer 120 and an inner layer 122, where the outer layer 120 forms the non-inflatable section 114 and is made of a non-expandable, non-electrically-conductive material of a first elastic modulus, while the inner layer 122 is formed of an expandable material of a different elastic modulus. A ring-shaped gap 124 is formed in the outer layer 120 to expose a portion of the inner layer 122, which forms the inflatable barrier 112. The gap 124 permits the material of the inner layer 122 to expand radially outwardly when suitable pressure is supplied by fluid "F" to thereby inflate the inflatable barrier 112, as illustrated in FIG. 6 depicting the inflatable barrier 112 in the expanded configuration.

Figure 7:
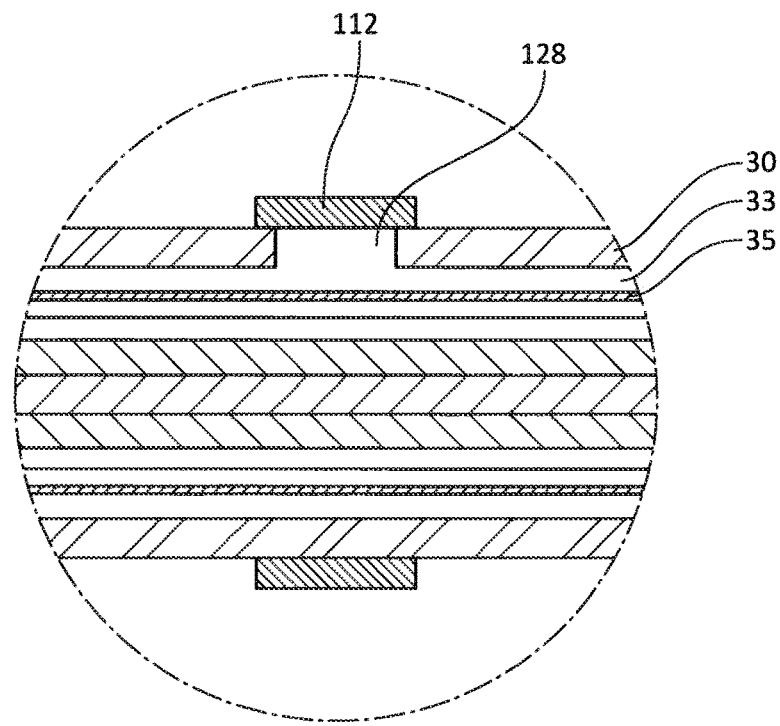
FIG. 7 is an enlarged, cross-sectional view of a portion of the probe assembly including an inflatable barrier in a collapsed configuration, in accordance with yet another embodiment of the present disclosure.
Figure 8:
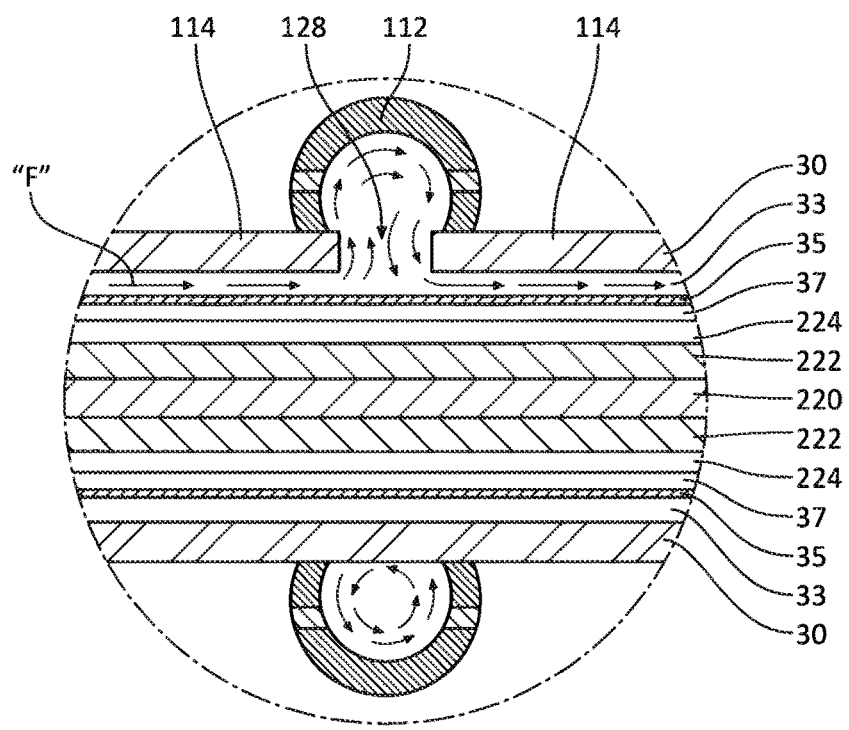
FIG. 8 is the enlarged, cross-sectional view of the portion of the probe assembly depicted in FIG. 7 including the inflatable barrier in an expanded configuration, in accordance with an embodiment of the present disclosure.

According to still another embodiment of the inflatable barrier 112, as depicted in FIG. 7, the inflatable barrier 112 is made of expandable material extending circumferentially around a section of the outer tubular member 30. Here, the outer tubular member 30 includes an aperture 128 over which the inflatable barrier 112 is disposed. The expandable material of the inflatable barrier 112 may be in the shape of a tube, so that when inflated due to pressurization supplied by fluid "F" as shown in FIG. 8, the tube forms a taurus around the outer tubular member 30. In another embodiment, the expandable material is a strip of material surrounding an entirety of the circumference of the outer tubular member 30, and the edges of the strip are sealingly coupled to the outer surface of the outer tubular member 30 to form a portion of the lumen 33.

Figure 10:
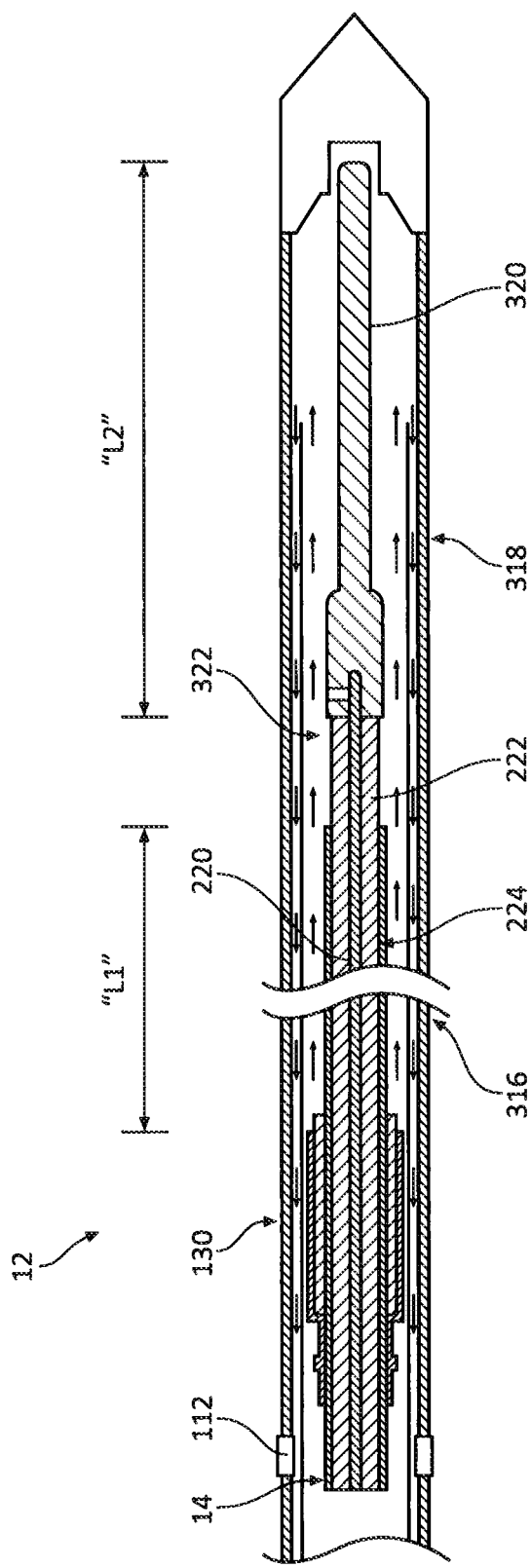
FIG. 10 is a cross sectional view of a portion of a probe assembly, in accordance with another embodiment of the present disclosure.

As noted briefly above, the inflatable barrier 112 is used to contain the steam that is generated as a by-product of an ablation procedure to prevent the fixation of holes by the medical device 10. In this regard, the inflatable barrier 112 is positioned at a location along the length of the antenna assembly 11 shown as part of the distal portion 12 for this purpose. With additional reference to FIG. 10, the antenna assembly 11 has a first radiating portion (for example, distal radiating section 318) and a second radiating portion (such as, proximal radiating section 316). The antenna assembly 11 is operably coupled by the feedline 14 to a transition assembly (not shown), which is adapted to electrically communicate, for example, transmit the microwave energy, from the cable assembly 15 to the feedline 14.

The feedline 14 may be any suitable transmission line, e.g., a coaxial cable. In an embodiment, the feedline 14 includes an inner conductor 220, an outer conductor 224 coaxially disposed around the inner conductor 220, and a dielectric material 222 disposed therebetween. The dielectric material 222 may be formed from any suitable dielectric material, e.g., polyethylene, polyethylene terephthalate, polyimide, or polytetrafluoroethylene (PTFE). The inner conductor 220 and the outer conductor 224 may be formed from any suitable electrically-conductive material. In some embodiments, the inner conductor 220 is formed from a first electrically-conductive material (e.g., stainless steel) and the outer conductor 224 is formed from a second electrically-conductive material (e.g., copper). Electrically-conductive materials used to form the feedline 14 may be plated with other materials, e.g., other conductive materials, such as gold or silver, to improve their properties, e.g., to improve conductivity, decrease energy loss, etc. The feedline 14 may have any suitable length defined between its proximal and distal ends. In accordance with various embodiments of the present disclosure, the feedline 14 is coupled at its proximal end to connector assembly 17 and coupled at its distal end to the antenna assembly 11 included as part of the distal portion 12. The feedline 14 is disposed at least in part within the inner tubular member 35.

The antenna assembly 11 includes a proximal radiating section 316 having a length "L1", a distal radiating section 318 including an electrically-conductive element 320 having a length "L2", and a feed point 322 located therebetween. In some embodiments, the proximal radiating section 316 may have a length "L1" in a range from about 0.05 inches to about 0.50 inches. The electrically-conductive element 320 may be formed of any suitable electrically-conductive material, e.g., metal such as stainless steel, aluminum, titanium, copper, or the like. In some embodiments, the electrically-conductive element 320 may have a length "L2" in a range from about 0.15 inches to about 1.0 inches. In an embodiment, the inflatable barrier 112 is disposed at a location proximal to proximal radiating section 316.

According to another embodiment, the antenna assembly 11 includes a balun 130 is disposed over the outer conductor 224 of the feedline 14 that may be located proximal to and spaced apart a suitable length from a feed point 322. The balun 130 generally includes a balun short, a balun insulator, and an electrically-conductive layer disposed around the outer peripheral surface of the balun insulator, or portions thereof. In some embodiments, a temperature sensor (not shown in) disposed in association with the balun 130. Here, in an embodiment, the inflatable barrier 112 is disposed adjacent to and proximal the balun 130. For example, the inflatable barrier 112 is located a few centimeters from the balun 130.

Referring now to FIGS. 1 and 2, during the ablation procedure, the probe assembly 20 initially is inserted into or placed at a desired location adjacent to target tissue. To permit the user to observe and better control probe assembly 20, one or more visualization techniques including ultrasound, computed tomography (CT), fluoroscopy, and direct visualization may be used to accurately guide probe 20 into the area of tissue to be treated. Probe 20 may be placed percutaneously or surgically, e.g., using conventional surgical techniques by surgical staff.

After placement, the inflatable barrier 112 then is inflated. In an example, according to various embodiments, the inflatable barrier 112 is inflated using coolant fluid. In an embodiment, the probe assembly 20 circulates coolant fluid "F", e.g., saline, water or other suitable coolant fluid, from a coolant source 52 of coolant supply system 50, which may be any suitable housing containing a reservoir of coolant fluid "F" and may maintain coolant fluid "F" at a predetermined temperature. For example, the coolant source 52 may include a cooling unit (not shown) capable of cooling the returning coolant fluid "F" from the distal portion 12 via the hub 40.

Coolant fluid "F" may have dielectric properties and may provide dielectric impedance buffering for the antenna assembly 11. Coolant fluid "F" composition may vary depending upon desired cooling rates and the desired tissue impedance matching properties. Various fluids may be used, e.g., liquids including, but not limited to, water, saline, perfluorocarbon, such as the commercially available Fluorinert® perfluorocarbon liquid offered by Minnesota Mining and Manufacturing Company (3M), liquid chlorodifluoromethane, etc. The coolant supply system 50 generally includes a first coolant path 16 leading from the coolant source 52 to the first port 41 (also referred to herein as the fluid inlet port), and a second coolant path 18 leading from the second port 42 (also referred to herein as the fluid outlet port) to the coolant source 52. In some embodiments, the first coolant path 16 includes a fluid-movement device (not shown) configured to move coolant fluid "F" through the first coolant path 16. Second coolant path 18 may additionally, or alternatively, include a fluid-movement device (not shown) configured to move coolant fluid "F" through the second coolant path 18, in an embodiment. Examples of coolant supply system embodiments are disclosed in commonly assigned U.S. Pat. No. 8,394,087 filed on Sep. 24, 2009, entitled "OPTICAL DETECTION OF INTERRUPTED FLUID FLOW TO ABLATION PROBE", and U.S. Pat. No. 9,101,344 entitled "RECIRCULATING COOLING SYSTEM FOR ENERGY DELIVERY DEVICE" the disclosure of which is incorporated herein by reference.

As a result of the movement of the coolant fluid "F" through the first coolant path 16, the fluid "F" enters first lumen 37 at the proximal end of the inner tubular member 35, flows through first lumen 37 to a distal portion of probe assembly 20 and enters second lumen 35. Due to the force exerted by the fluid "F" against an inner surface of inflatable barrier 112, inflatable barrier 112 expands into the expanded configuration.

Figure 2A:
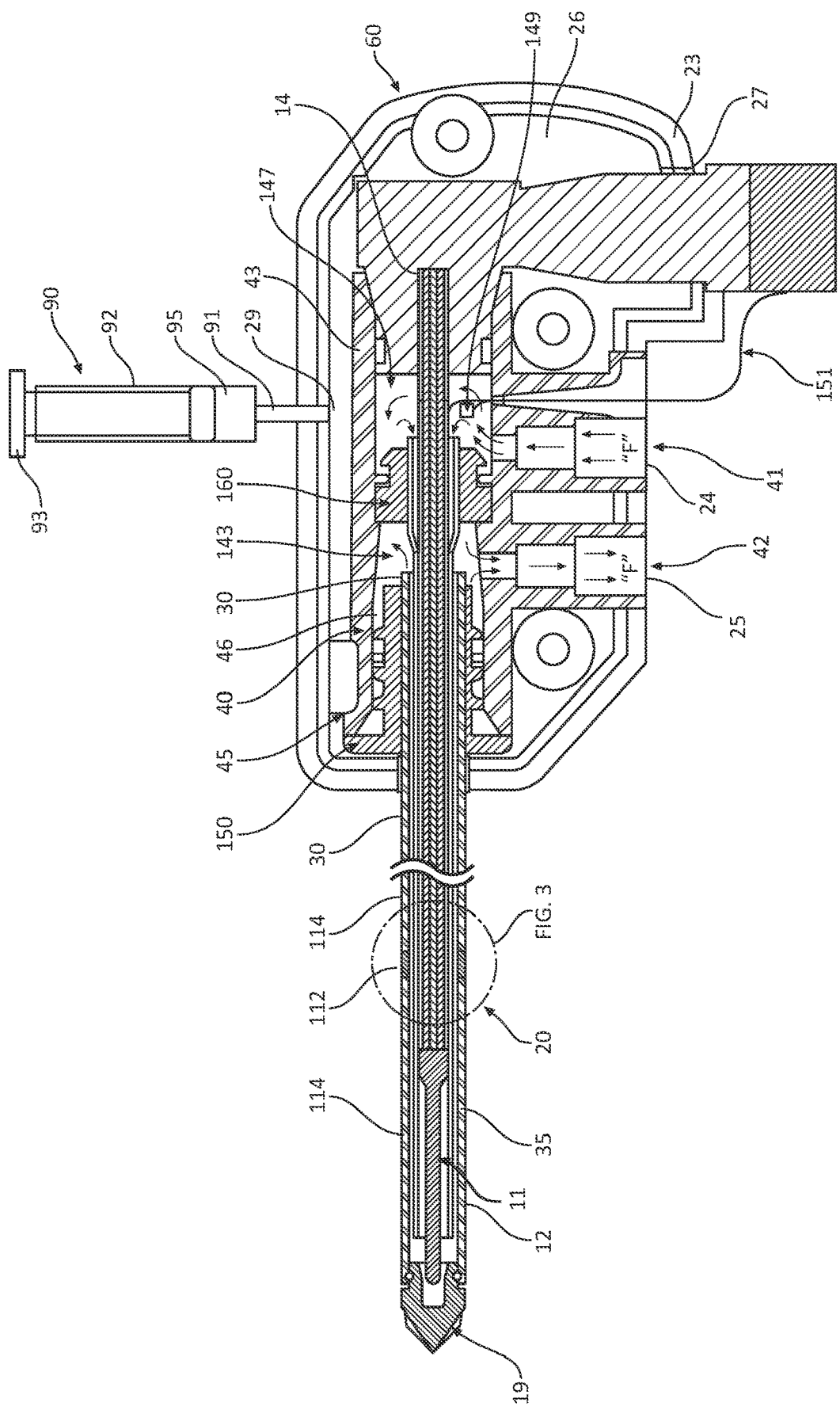
FIG. 2A is a longitudinal cross-section view of a medical device for use in the microwave ablation system of FIG. 1, in accordance with an embodiment of the present disclosure.

According to another embodiment, the inflatable barrier 112 is inflated using gas or fluid other than coolant fluid "F". In accordance with another embodiment of the present disclosure, the inflatable barrier is inflated using an air pump 90. With reference to FIGS. 1 and 2A, in this regard, an opening 29 for receiving a connector of the air pump 90 is included in the handle body 23 and includes a sealing element to maintain the handle-body chamber 26 substantially airtight. The air pump 90 may be configured as a syringe having a barrel 92 defining a chamber 95 within which a plunger 93 is inserted. A shaft or tip 91 extends from the barrel 92 and is configured to be inserted through the opening 29 to provide fluid communication between barrel chamber 95 and handle-body chamber 26. As is typically the case during operation of a syringe, when the plunger 93 is actuated, fluid (for example, a gas or liquid) can be introduced into or drawn out of barrel chamber 95, which in turn is moved into and out of the handle-body chamber 26.

Figure 2B:
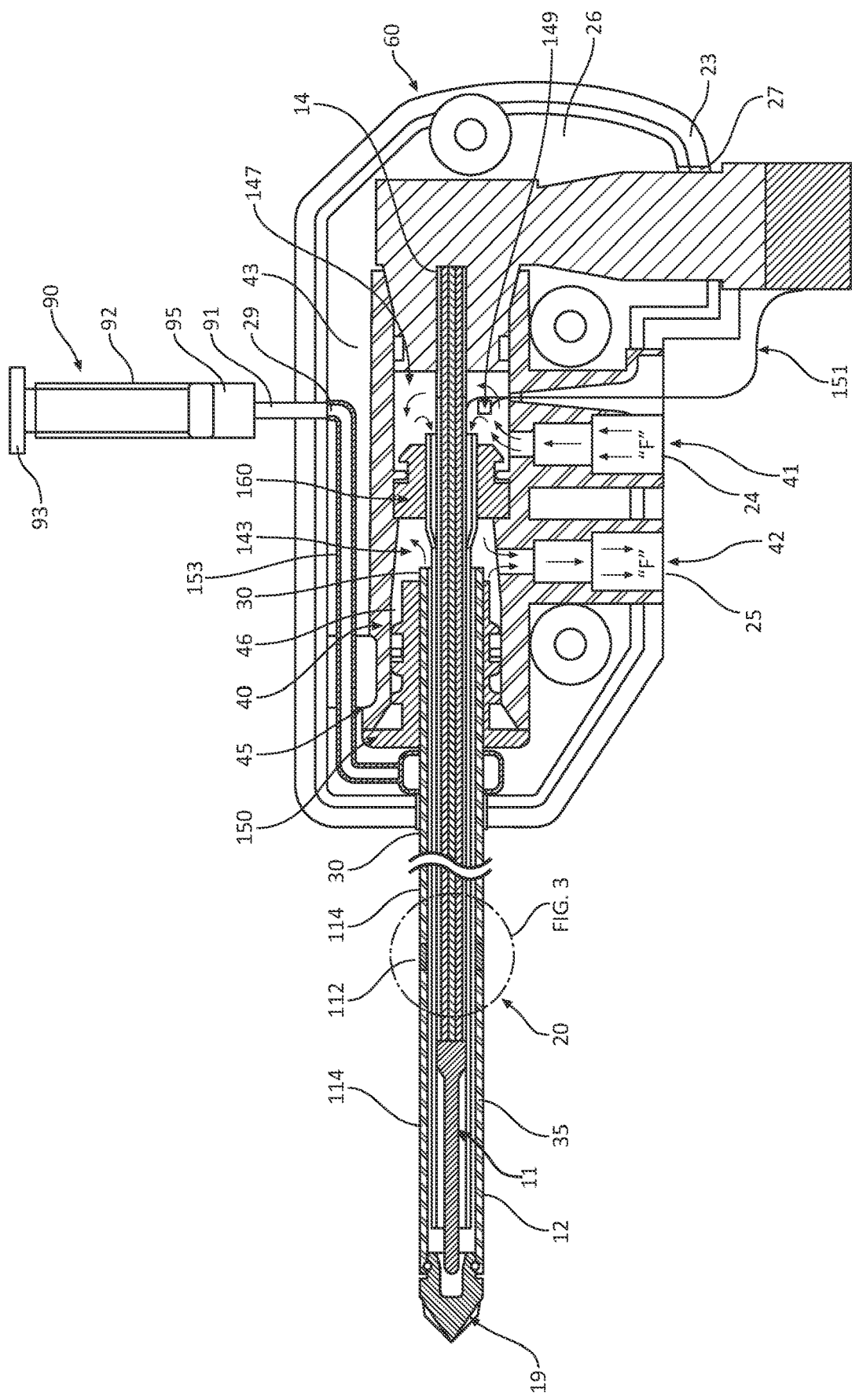
FIG. 2B is a longitudinal cross-section view of a medical device for use in the microwave ablation system of FIG. 1, in accordance with another embodiment of the present disclosure.
Figure 9A:
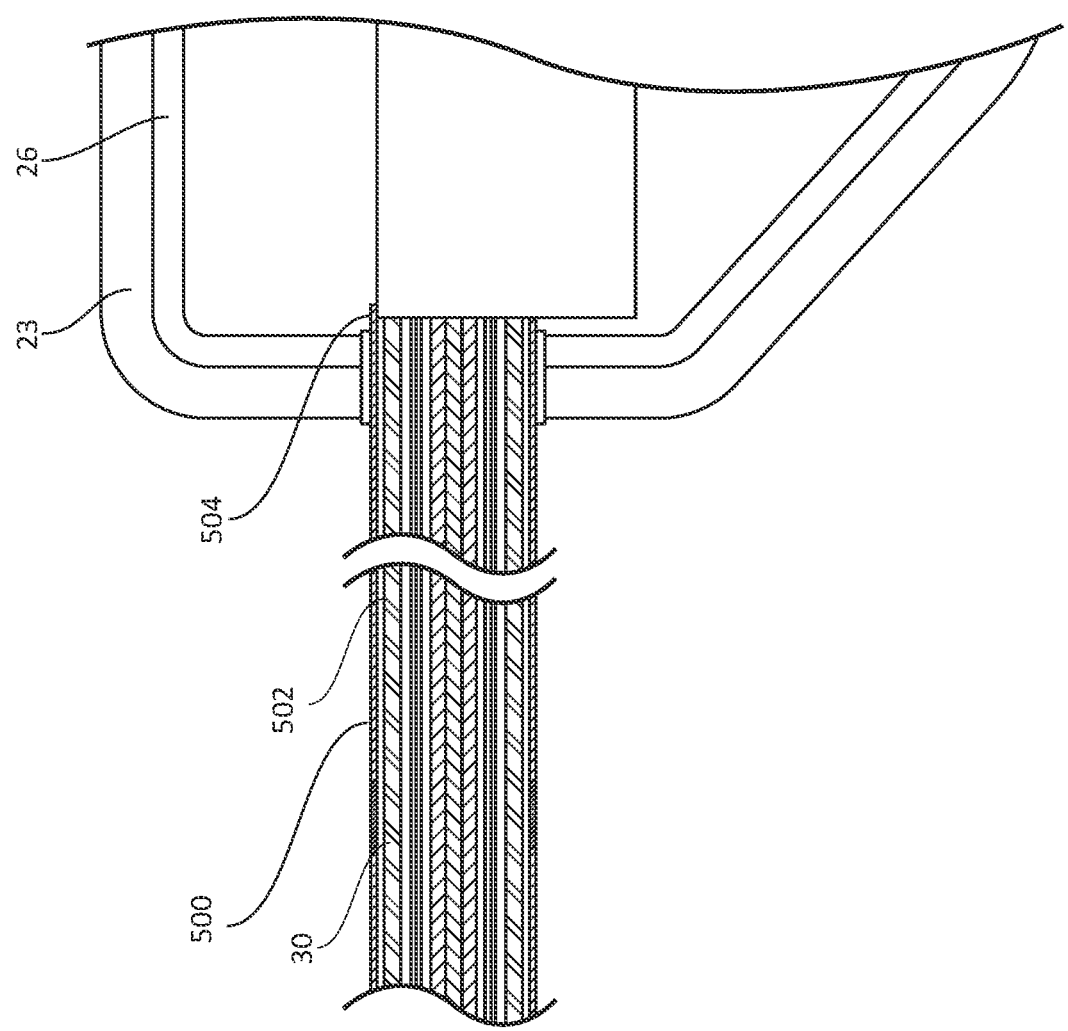
FIG. 9A is a cross sectional view of a portion of a probe assembly extending from a hub, in accordance with an embodiment of the present disclosure.
Figure 9B:
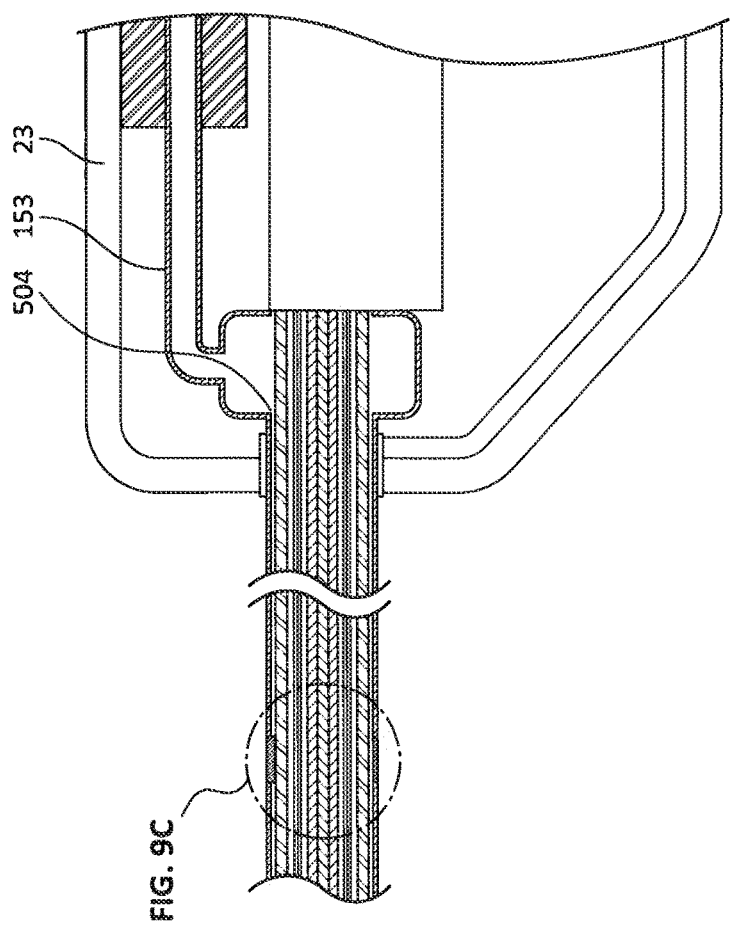
FIG. 9B is a cross sectional view of a portion of a probe assembly extending from a hub, in accordance with another embodiment of the present disclosure.
Figure 9C:
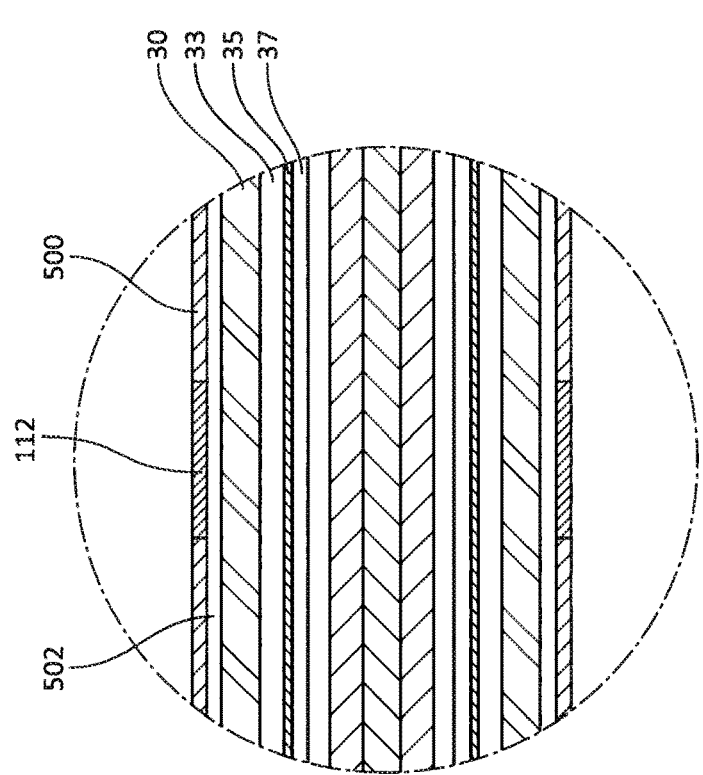
FIG. 9C is an enlarged, cross-sectional view of a portion of the probe assembly of FIG. 9B including an inflatable barrier in a collapsed configuration, in accordance with still yet an embodiment of the present disclosure.

Turning to FIG. 9A, in another embodiment, the inflatable barrier is formed as part of an outer sheath 500 disposed on the outer tubular member 30. The outer sheath 500 extends along at least a portion of a length of the outer tubular member 30 such that a proximal portion 504 of the outer sheath 500 is coupled to the hub body 23 and in communication with the handle-body chamber 26 and a distal portion of the outer sheath 500 extends just short of a distal portion of the antenna assembly 11 to thereby define a lumen 502 between the outer sheath 500 and the outer tubular member 30. In an embodiment, the outer sheath 500 may include an enclosed distal end and the proximal end of the outer sheath 500 may extend into the hub body 23 to form a leak tight seal therewith. In another embodiment, the distal portion of the outer sheath 500 is sealingly attached to an outer surface of the outer tubular member 30, while the proximal end of the outer sheath 500 is coupled to hub body 23 in a manner suitable for maintaining the lumen 502 leak tight. No matter the particular configuration, the outer sheath 500 includes the inflatable barrier 112 and may be configured in a manner similar to the embodiments of the outer tubular member 30 as described in conjunction with FIGS. 2A-8. Although depicted in FIGS. 1, 2A, and 9A as delivering the pumped fluid through the hand-body chamber 26, the pump 90 may be alternatively configured, as shown in FIGS. 2B, 9B, and 9C such that a tube 153 is included to provide communication between the pump 90 and the inflatable barrier. The tube 153 includes a proximal end portion inserted through opening 29 and a distal end portion that is either coupled to or integrally formed with the outer sheath 500 of the inflatable barrier to thereby communicate with the lumen 502.

With reference to FIGS. 1, 2A, and 9A, for example, in an embodiment in which a pump 90 is included, the barrel chamber 95 is filled with fluid and the plunger 93 is inserted. The tip 91 extending from the barrel 92 is inserted through the opening 29 of the hub assembly 23 to provide fluid communication between the barrel chamber 95 and the handle-body chamber 26. The plunger 93 is actuated toward the tip 91 and the fluid is moved from the barrel chamber 95 into the handle-body chamber 26. As the plunger 93 is inserted further into the barrel chamber 95, the fluid enters the lumen 502. Due to the force exerted by the fluid against an inner surface of the outer sheath 500, the inflatable barrier 112 expands into the expanded configuration.

No matter the manner by which inflatable barrier 112 is expanded, while in the expanded configuration, the inflatable barrier 112 exerts a force against surrounding tissue to thereby prevent the probe assembly 20 from becoming displaced from its initial location.

After the inflatable barrier 112 is expanded, energy is supplied to the probe assembly 20 to ablate the tissue. For example, the operation of inflation of the inflatable barrier 112 and the supply of energy may occur automatically with the powering off the pump. During ablation, heat from the ablation of the tissue may generate steam, which is maintained within a predefined area within the tissue via a barrier created by the inflatable barrier 112. In this way, the steam resulting from the ablation is prevented from traveling down the length of the probe assembly 20, reducing a likelihood of the formation of a thermally fixed hole within the tissue.

When the tissue ablation is complete, the probe assembly 20 is removed from the patient. For example, the inflatable barrier 112 is deflated into a contracted configuration. In an embodiment, the coolant source 52 discontinues supplying coolant fluid "F" thereby depressurizing the lumen 35 and causing the inflatable barrier 112 to deflate, and the pump is run a bit to remove the coolant fluid "F" from the system with the inlet shut. In another embodiment, the plunger 93 of the air pump 90 is actuated away from the tip 91 to thereby withdraw fluid from the lumen 35, which results in deflating the inflatable barrier 112.

Figure 11:
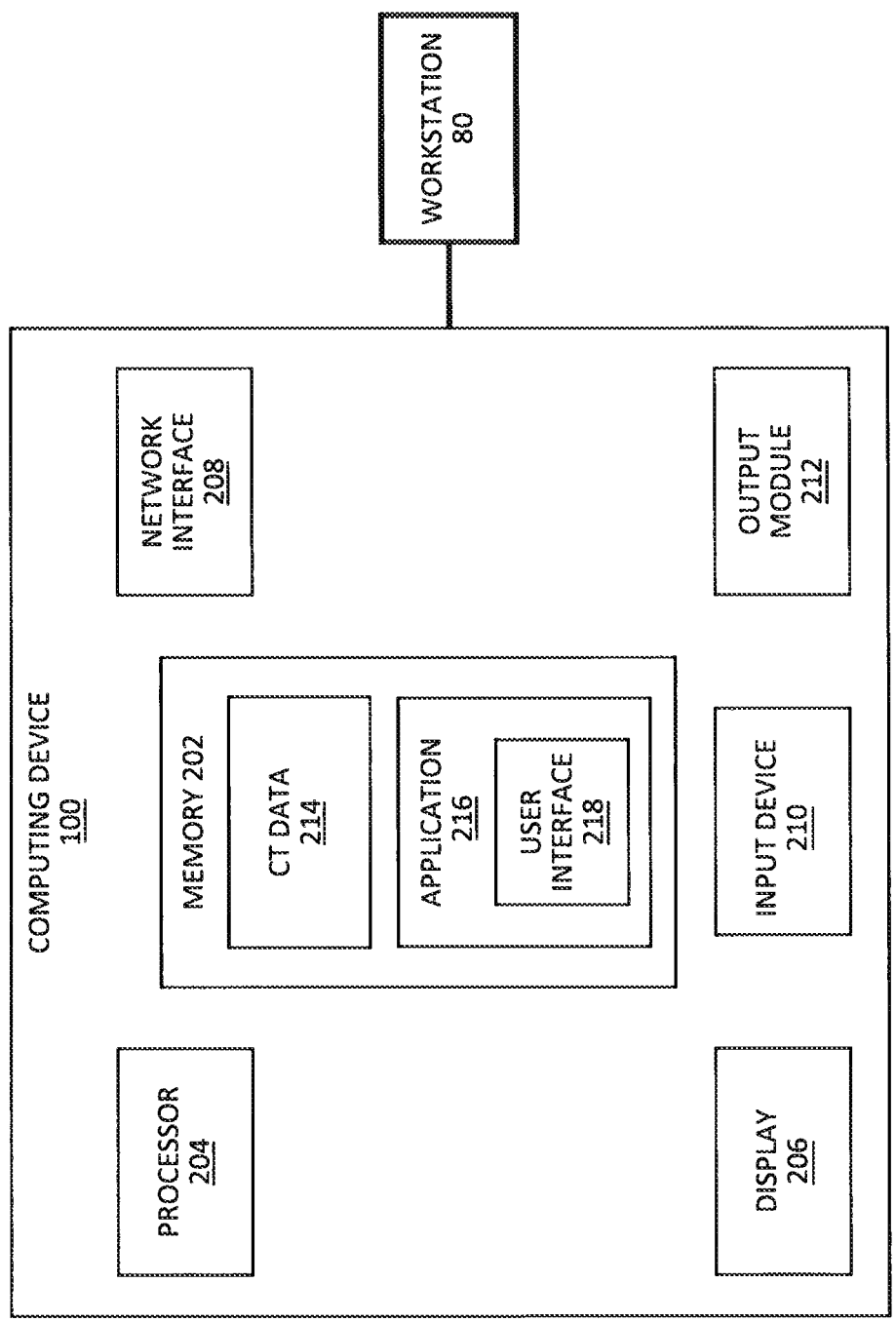
FIG. 11 is a block diagram of a computing device that may be implemented as part of the microwave ablation system, in accordance with an embodiment of the present disclosure.

In other embodiments, a computing device 100 may be operated independently to control inflation/deflation of the inflatable barrier 112 via the microwave generator 28 and/or energization of the probe assembly 20 via the microwave generator 28 and/or control the coolant supply system 50. For example, as shown in FIG. 11, computing device 100 may include a display 206 having a control screen which enables a clinician to control the microwave generator 28 and/or the coolant supply system 50 without interacting directly with either component. The clinician may use the computing device 100 to configure settings for the microwave ablation procedure, which includes preconfiguring output wattages and ablation zones for each target to be ablated during the procedure, as well as settings related to providing power to the coolant source 52 or pumps associated with the coolant source 52 for delivering coolant fluid "F", detecting when the inflatable barrier 112 is fully expanded, delivering energy to the antenna assembly 11 when the inflatable barrier 112 is detected as fully expanded, deflating the inflatable barrier 112 when completion of the ablation procedure is detected, and providing indication that the probe assembly 20 can be removed from the patient.

The computing device 100 includes a memory 202, a processor 204, display 206, a network interface 208, an input device 210, and/or an output module 212.

The memory 202 includes any non-transitory computer-readable storage media for storing data and/or software that is executable by the processor 204 and which controls the operation of the workstation 80. In an embodiment, the memory 202 may include one or more solid-state storage devices such as flash memory chips. Alternatively or in addition to the one or more solid-state storage devices, the memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by the workstation 80.

The memory 202 may store an application 216. The application 216 may, when executed by the processor 204, cause the display 206 to present the user interface 218. The network interface 208 may be configured to connect to a network such as a local area network (LAN) consisting of a wired network and/or a wireless network, a wide area network (WAN), a wireless mobile network, a Bluetooth network, and/or the internet. The input device 210 may be any device by means of which a user may interact with the workstation 80, such as, for example, a mouse, keyboard, foot pedal, touch screen, and/or voice interface. The output module 212 may include any connectivity port or bus, such as, for example, parallel ports, serial ports, universal serial busses (USB), or any other similar connectivity port known to those skilled in the art.

As it is used in this description, "length" may refer to electrical length or physical length. In general, electrical length is an expression of the length of a transmission medium in terms of the wavelength of a signal propagating within the medium. Electrical length is normally expressed in terms of wavelength, radians or degrees. For example, electrical length may be expressed as a multiple or sub-multiple of the wavelength of an electromagnetic wave or electrical signal propagating within a transmission medium. The wavelength may be expressed in radians or in artificial units of angular measure, such as degrees. The electrical length is in general different from the physical length. By the addition of an appropriate reactive element (capacitive or inductive), the electrical length may be made significantly shorter or longer than the physical length.

Various embodiments of the presently disclosed energy-delivery device with a fluid-cooled probe assembly including a balun are suitable for microwave or RF ablation and for use to pre-coagulate tissue for microwave or RF ablation-assisted surgical resection. Although various methods described hereinbelow are targeted toward microwave ablation and the complete destruction of target tissue, it is to be understood that methods for directing electromagnetic radiation may be used with other therapies in which the target tissue is partially destroyed or damaged, such as, for example, to prevent the conduction of electrical impulses within heart tissue. In addition, the teachings of the present disclosure may apply to a monopole, dipole, helical, or other suitable type of microwave antenna or RF electrode.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A microwave ablation device comprising:
   a feedline being in electrical communication with an energy source;
   an antenna assembly coupled to the feedline and including a radiating portion;
   an outer tubular member defining a lumen, through which the feedline at least partially extends, and an aperture; and
   an inflatable barrier operably coupled to an outer surface of the outer tubular member proximal to the radiating portion of the antenna assembly and over the aperture defined by the outer tubular member, the inflatable barrier being expandable to extend the lumen to a region between an inner surface of the inflatable barrier and the outer surface of the outer tubular member.

2. The microwave ablation device of claim 1, wherein: the outer tubular member is formed of a first material and the inflatable barrier is formed a second material, wherein the second material has a higher elastic modulus than the first material.

3. The microwave ablation device of claim 1, further comprising a hub including a port configured to be coupled to a cooling pump to pressurize the lumen defined by the outer tubular member, wherein the inflatable barrier is configured to expand in response to pressurization of the lumen, and the inflatable barrier is configured to deflate in response to depressurization of the lumen.

4. The microwave ablation device of claim 1, further comprising an outer sheath extending along a portion of the outer tubular member.

5. The microwave ablation device of claim 4, further comprising a hub including a port configured to be coupled to a pump to pressurize the lumen defined by the outer sheath, wherein the inflatable barrier is configured to expand in response to pressurization of the lumen, and the inflatable barrier is configured to deflate in response to depressurization of the lumen.

6. The microwave ablation device of claim 1, wherein the lumen extends to a distal end of the outer tubular member.

7. The microwave ablation device of claim 1, wherein the inflatable barrier surrounds an outer circumference of the outer surface of the outer tubular member.

8. The microwave ablation device of claim 1, wherein outer edges of the inflatable barrier are sealingly coupled to the outer surface of the outer tubular member.

9. The microwave ablation device of claim 1, wherein the lumen extends distally beyond the inflatable barrier along a longitudinal axis defined by the outer tubular member.

10. A system for performing a microwave ablation procedure, the system comprising:
an electrosurgical generator;
a cooling fluid pump; and
a microwave ablation device including:
a cable assembly operably coupled to the electrosurgical generator,
a feedline being in electrical communication with the cable assembly,
an antenna assembly coupled to the feedline and including a radiating portion,
an outer tubular member defining a lumen, through which the feedline at least partially extends, and an aperture, and
an inflatable barrier disposed on an outer surface of the outer tubular member proximal to the radiating portion of the antenna assembly and over the aperture defined by the outer tubular member, the inflatable barrier being expandable to extend the lumen to a region between an inner surface of the inflatable barrier and the outer surface of the outer tubular member.

11. The system of claim 10, wherein
the microwave ablation device further includes a hub including a port in communication with the lumen defined by the outer tubular member, and the cooling fluid pump is configured to pressurize the lumen defined by the outer tubular member, wherein the inflatable barrier is configured to expand in response to pressurization of the lumen, and the inflatable barrier is configured to deflate in response to depressurization of the lumen.

12. The system of claim 11, further comprising:
a computing device including a processor and a memory storing instructions which, when executed by the processor, cause the computing device to:
start the cooling fluid pump to pressurize the lumen and thereby expand the inflatable barrier,
detect a pressure within the lumen, and
generate electrosurgical energy using the electrosurgical generator to deliver microwave energy to the feedline, based upon the detected pressure within the lumen being greater than a threshold pressure.

13. The system of claim 10, wherein:
the microwave ablation device further includes an outer sheath extending along a portion of the outer tubular member, and
the system further comprises a hub including an opening in communication with a lumen defined by the outer sheath, and
a pump coupled to the hub configured to pressurize the lumen defined by the outer sheath, wherein the inflatable barrier is configured to expand in response to pressurization of the lumen defined by the outer sheath, and the inflatable barrier is configured to deflate in response to depressurization of the lumen defined by the outer sheath.

14. The system of claim 13, further comprising:
a computing device including a processor and a memory storing instructions which, when executed by the processor, cause the computing device to:
start the pump to pressurize the lumen defined by the outer sheath and thereby expand the inflatable barrier,
detect a pressure within the lumen defined by the outer sheath, and
generate electrosurgical energy using the electrosurgical generator to deliver microwave energy to the feedline, based upon the detected pressure within the lumen defined by the outer sheath being greater than a threshold pressure.

15. The system of claim 14, wherein the memory stores further instructions which, when executed by the processor, cause the computing device to, deflate the inflatable barrier based upon a detection of the microwave energy not being delivered to the feedline to thereby cause the lumen defined by the outer sheath to be de-pressurized.

16. The system of claim 14, wherein the pump includes a syringe.

17. The system of claim 10, wherein the lumen extends to a distal end of the outer tubular member.

18. The system of claim 10, wherein the inflatable barrier surrounds an outer circumference of the outer surface of the outer tubular member.

19. The system of claim 10, wherein outer edges of the inflatable barrier are sealingly coupled to the outer surface of the outer tubular member.

20. The system of claim 10, wherein the lumen extends distally beyond the inflatable barrier along a longitudinal axis defined by the outer tubular member.

* * * * *